United States Patent [19]

Bailey

[11] 4,365,956
[45] Dec. 28, 1982

[54] CLEANING CUP

[75] Inventor: Ronald L. Bailey, St. Peters, Mo.

[73] Assignee: Young Dental Manufacturing Company, Hazelwood, Mo.

[21] Appl. No.: 953,474

[22] Filed: Oct. 23, 1978

[51] Int. Cl.³ .......................... A61C 1/05; A61C 3/06
[52] U.S. Cl. .................................... 433/115; 433/125
[58] Field of Search ................. 32/59, 27, 26, 29, 30, 32/31, 48; 433/115, 125

[56] References Cited

U.S. PATENT DOCUMENTS

| | | | |
|---|---|---|---|
| 1,678,097 | 7/1928 | Andresen | 433/115 |
| 1,837,938 | 12/1931 | Young | 32/59 |
| 2,005,849 | 6/1935 | Skinner | 32/27 |
| 2,469,261 | 5/1949 | Cooper | 32/59 |
| 3,436,830 | 4/1969 | Richmond | 32/59 |
| 3,478,433 | 11/1969 | Richmond | 32/59 |

FOREIGN PATENT DOCUMENTS 355653 10/1973 Sweden ................................. 32/59

Primary Examiner—Gene Mancene
Assistant Examiner—John J. Wilson
Attorney, Agent, or Firm—Rogers, Eilers & Howell

[57] ABSTRACT

A dental tool and handpiece, wherein the tool has a projecting cylindrical, flexible flange extending into a cylindrical recess in the handpiece and sealable thereinto by centrifugal force. Various forms are illustrated. The operation of the flange is independent of the attaching means for the tool, and end forces on the tool are not transmitted through the flange, but rather are transmitted through a driven shaft on which the tool is mounted, thence through a driven gear having a thrust bearing engagement with the closed end of the head.

9 Claims, 5 Drawing Figures

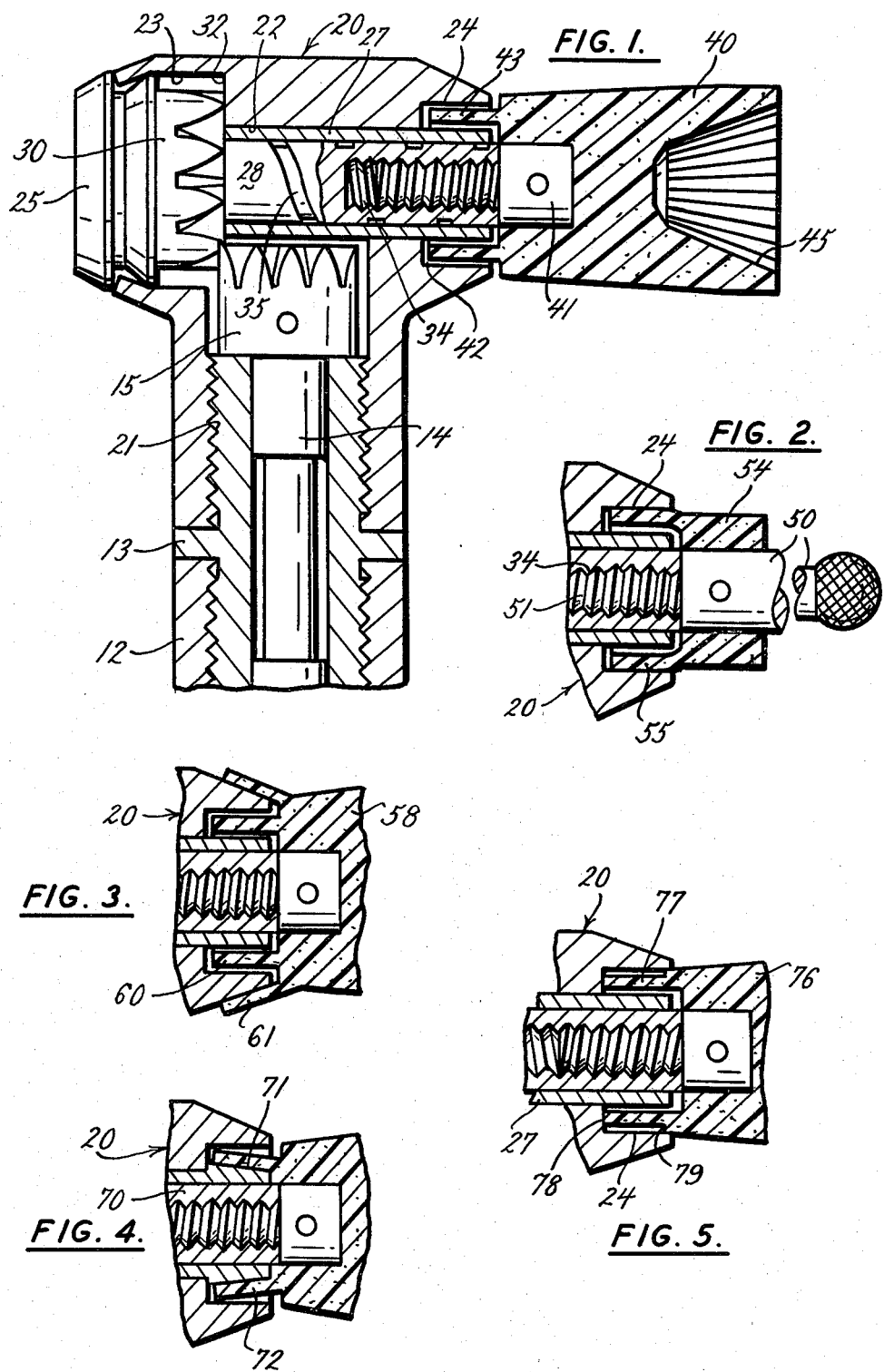

CLEANING CUP

BACKGROUND OF THE INVENTION

A broad object of the invention is a compact dental handpiece or prophylaxis angle and dental tool combination that minimizes the passage of material such as abrasives from the open or tool-receiving end to the rotating parts and closed end.

Other dental handpieces are shown in Richmond U.S. Pat. No. 3,436,830, Baily 4,014,099, Fernald 1,170,523 and Heatherington 3,978,586 and the art cited in them. Cooper U.S. Pat. No. 2,469,261 purports to illustrate an arrangement by which a rubber cup can seal by compression, but the disclosure is different in that, among other things, the driving mechanism between the shaft and the rubber cup is part of the same mechanism that is supposed to give the sealing arrangement.

Objects of the present invention therefore include broadly the combination of a cross head for a dental handpiece and a dental tool that minimizes having granular or abrasive material reach the moving parts where it could abrade them. A specific object is a dental tool with a flexible flange or skirt means engageable in a cylindrical opening wherein it may seal by centrifugal force, and which is independent of the attachment of the tool to the handpiece.

A further object is to provide a dental tool with such a flexible flange seal that does not subject the sealing means to the thrust forces in use.

Further objects include the provision of a skirt arrangement that seals both when the instrument is at rest and when it is spinning. Specifically, it is an object to provide this with a single skirt. And more specifically it is an object to provide a three-point seal.

IN THE DRAWINGS:

FIG. 1 is a diametrical section through the end of a dental handpiece with a typical dental tool in place, the parts being at rest;

FIG. 2 is a fractional section showing the action of the flexible flange during rotation of the dental tool, the tool in this view being a burr;

FIG. 3 is a similar fractional view in a modified form of flanges for dental tools affording a double seal arrangement;

FIG. 4 is a further modification of the seal arrangement for a dental tool; and

FIG. 5 is an additional modification, showing multiple seal points.

PREFERRED EMBODIMENT OF THE INVENTION

Referring first to FIG. 1, the dental handpiece or prophylaxis angle combination comprises a sleeve 12 shown broken away adjacent its outer end. This showing does not include the extended handle portion broken away. The drawing is enlarged, a typical diameter of this outer end being about 9/32" (0.714 cm.). The sleeve 12 is internally threaded at its end to receive a tubular double-ended threaded drive shaft bearing 13 that receives a drive shaft 14 driven by an electric or air motor (not shown). A drive gear 15 is fixed to the outer end of the drive shaft and is rotated by the shaft. The end of the gear 15 bears on the end of the drive shaft bearing 13.

A cross head 20 has a longitudinal bore 21 with an internally threaded end mountable over the projecting externally threaded end of the bearing 13. The bore 21 receives the gear 15. The head can thus be removed from the handle by being unscrewed, the gear 15 being capable of passing through the threaded opening. The head 20 also has a transverse counterbore 22 into which the bore 21 connects. This counterbore 22 at the left (FIG. 1) has an enlargement 23 and at its right end has an enlargement 24. The end of the bore at the left of the drawing is closed by a cap 25. The cap is peripherally grooved to be fixed in place by having the rim of the recess 23 swedged over into the groove. The capped end of the bore is here designated as the closed end.

The transverse bore 22 receives a long fixed cylindrical bearing 27 of appropriate bearing metal, that extends from a recess 23 to the opposite or open end of the head 20. It projects across the enlarged bore 24 at that end. It is designed to be long for a purpose to appear.

A driven shaft or burr tube 28 is fitted within the bearing 27 with a close rotating fit, and is secured to a driven gear 30 within the bore enlargement or recess 23. The outer (left, FIG. 1) end of the gear 30 and the inner face of the cap 25 have flat interfaces that provide a thrust bearing for the driven gear assembly and the dental tool.

The cap 25 also seals the end of the head 20. The teeth on the driven gear 30 are bevelled, and the hub inside the teeth abuts the end surface 32 of the bore enlargement 23 and the end of the bearing 27. Thus the gear 30 and the burr tube 28 are retained rotatably in the head 20 between the cap 25 and the surface 32, with the driven gear 30 meshing with the driving gear 15.

The burr tube shaft 28 has a threaded closed end socket 34 to receive dental tools or instruments to be operated by the handpiece.

Preferably the burr tube or driven shaft 28 is provided on its outer surface with spiral grooves 35 for a purpose to appear. These grooves may open into the counterbore enlargement 23 at one end, and do open into the opposite end of the burr tube.

This dental handpiece is adapted to be used with all of the usual kinds of dental tubes or instruments such as burr tubes, rubber cups, disk holders and the like, that are provided with flexible flanges such as will be described. And such is shown in FIG. 1. It comprises a rubber cup 40 of typical flexible, resilient, material and outer shaping, permanently mounted upon a metal core 41 that has an externally threaded shank by which it is attached to internal threading of the closed end socket 34 in the shaft 28.

In the illustrated rubber cup, there is an integral cylindrical flange 43 of the flexible rubber or plastic material, designed to fit within the cylindrical groove 42 formed by the enlargement 24 of the counterbore 22 around the outside of the bearing 27.

The rubber cup may preferably be made of live rubber. It has the usual generally frusto-conical recess 45. The flange or skirt 43 can have a uniform thickness as shown in FIG. 1, of approximately 0.016 inches (0.041 cm) where the internal diameter is 0.155 inches (0.394 cm.) and the external diameter is 0.187 inches (0.475 cm). The skirt may typically be about 3/32" (0.238 cm) long.

Use

In use, the tool, here shown as the rubber cup, is mounted with its externally threaded insert-molded attaching pin secured in the internally threaded closedend recess 34 of the driven shaft 28. The instrument, when used by the dentist against the teeth, applies a thrust force to the left in FIG. 1, while centrifugal force acts upon the flexible flange or skirt 43, the rotating speeds being up to about 1500 r.p.m.

The rotation causes the flexible skirt 43 to spread outwardly, increasing its diameter, and engaging the wall of the recess 24 where it forms a seal restricting or obstructing the passage of granular or other material from the outside of the cup member 40 to the bearing 22. FIG. 2 illustrates the centrifugal sealing by such a skirt. It blocks the flow of granular or other material to the rotating parts.

In the foregoing action there is little of the thrust force applied to the skirt 43 because it is taken up by the main portion of the cup 40 and transmitted to the embedded metal insert 41 and thence to the shaft 28 and by way of the gear 30 and its interface with the cap 25 to that cap. This arrangement enables the skirt 43 to be as flexible as desired. Also the attaching means cannot transmit foreign matter to the gearing.

The dental tool may be other than the rubber cup as for example, a burr, as shown in FIG. 2. The burr has its shaft 50 with the projecting threaded end 51 to engage in the internally threaded socket 34 of the head 20.

A rubber flanged member 54 is molded sealingly around or chemically bonded to the burr shank and is pinned to it as shown, with the skirt 55 engaging against the wall of the recess 24 during rotation. In this case, the foreign matter is prevented from going around the skirt because of the effect of centrifugal force in spreading the skirt to the outer wall of the recess 24 as shown in FIG. 2. It is also prevented from passing between the rubber ring 54 and the shank of the burr by virtue of the molding of the rubber about the shank.

FIG. 3 shows a modification in which the rubber member 58 has a skirt 60 corresponding to the skirt 43 of FIG. 1 and the skirt 55 of FIG. 2. In addition, it has a normally cylindrical outer skirt 61 that bears inwardly on the outer tapering end of the head 20 when the instrument is at rest. This aids in keeping the foreign matter from entering the moving parts and bearing areas when the instrument is inserted into the mouth and before rotation is started. Once rotation is started, centrifugal force causes the skirt 60 to effect the seal as shown in FIG. 2, while the outer skirt 61 may be subject to centrifugal force to break its seal. This is not normally a problem because the length of the skirts 60 and 61 is only approximately 3/32" (0.238 cm) long.

A further modification is shown in FIG. 4. There the bearing 70 that corresponds to the bearing 22 of FIG. 1 is provided with a tapered end 71 and this deflects the normally cylindrical skirt 72 that corresponds to the skirt 43 so that there is a sealing effect when the machine is at rest, as well as when it is operating. This arrangement combines into the one skirt the effect of the two skirts 60 and 61 of FIG. 3 as the skirt 72 seals against the taper 71 when the machine is at rest but is caused by centrifugal force to engage and seal against the wall 24 of the head 20 when the machine is operating.

FIG. 5 shows a still further modification. There the head 20 is as before and has the bearing 27 as before. In this case the rubber member 76 has a skirt 77 that is long enough to have its end engage the end wall 78 of the recess 24 at all times and to provide a seal thereat. Also the skirt 77 is externally recessed or reduced in diameter toward its open end to provide an edge or shoulder 79 that engages the outer end of the head 20 just within the wall 24 at all times. This provides a second seal adjacent the rim 79. When centrifugal force is developed by operation of the machine, the remainder of the skirt 77 flexes outwardly and seals against the wall 24. It will be understood that the sealing adjacent rim 79 could be attained in other ways, such as by tapering the outer surface of the skirt 77 to contact the outer edge of the recess 24, or the shoulder of the skirt could be positioned to engage the end of the head 20. In all such cases, a static seal is obtained as will as a seal during running of the machine.

What I claim is:

1. In a dental device: a handpiece having a head; a shaft rotatably mounted in the head, the head being open at one end to expose the shaft for connection of a dental tool to the shaft; a circular recess in the open end of the head concentric with the shaft; a dental tool mounted on the head, connecting means between the tool and the shaft for rotation of the tool by the shaft; a flexible rubber-like skirt on the tool and unitary therewith, the skirt being separate from the connecting means and the skirt projecting from the end adjacent to the connecting means so that the connecting means transmits thrust forces from the tool to the shaft independently of the skirt, the skirt extending into the recess to engage the circular wall thereof sealingly by centrifugal force during rotation of the tool, said connecting means allowing the tool to be detached and attached to the shaft so that the skirt moves freely within the circular recess during attachment and detachment of the tool to the shaft to be free from contact with the wall of the circular recess and with the shaft when the tool is static relative to the head.

2. In the rotary dental tool of claim 1: static sealing means on the dental tool to seal against the hand-piece when the tool is static, in addition to the seal by centrifugal forces.

3. In the rotary dental tool of claim 2: the static sealing means including an additional skirt integral with and extending from the tool adjacent the first skirt, and engageable with the outside of the head when the machine is inoperative.

4. In the rotary dental tool of claim 1: the skirt having a portion of its external diameter great enough when static to seal against the internal wall, the other portions smaller than that diameter, whereby the first said portions may seal against the wall under static conditions and the other portions may seal against the wall by centrifugal force during rotation.

5. In the rotary dental tool of claim 1: the skirt having an end surface adapted for sealing against a complementary end surface in the head.

6. In the rotary dental tool of claim 5: the skirt having an outer surface for having an engagement with the internal wall when the tool is static.

7. In the rotary dental tool of claim 6: the skirt having its outer surface sized to be out of static engagement with the internal wall except adjacent its base, and providing the remainder of the skirt to be subject to centrifugal force for engaging the wall.

8. A dental device comprising a dental handpiece having a head which has a cylindrical opening and a larger cylindrical recess concentric with the opening at one end; a shaft rotatable in the head; a rotary dental tool; securing means at one end of the tool for mounting it on the shaft; a cylindrical sleeve bearing extending into the opening and projecting through the recess to cause the recess to have annular shape, the shaft being rotatably mounted in the bearing; the securing means on the dental tool comprising interfitting members between the shaft and the tool, adapted to transmit thrust forces from the tool to the shaft; means in the head to receive the thrust forces on the shaft; sealing means comprising a flexible continuous skirt of rubber-like material forming an integral part of the tool and projecting from the end adjacent to the securing means but being separate from the securing means, the skirt extending into the annular recess outside the bearing for rotation therein, whereby when the tool is mounted on the shaft and rotated, centrifugal force may spread the skirt into close engagement with the internal wall to restrict passage of foreign matter between them.

9. A dental device for use with a dental handpiece that has a shaft rotatable in a head, the shaft being adapted to receive a dental tool, and a head which has an internal cylindrical wall adjacent to the end of the shaft; the invention comprising: a rotary dental tool; securing means at one end of the tool for mounting it on the shaft; sealing means comprising a flexible continuous skirt of rubber-like material forming an integral part of the tool and projecting from the end adjacent to but separate from the securing means, whereby when the tool is mounted on the shaft and rotated, centrifugal force may spread the skirt into close engagement with the internal wall to restrict passage of foreign matter between them; and static sealing means on the dental tool to seal against the handpiece when the tool is static, in addition to the seal by centrifugal forces, the static sealing means including an additional skirt integral with and extending from the tool adjacent the first skirt, and engagable with the outside of the head when the machine is inoperative.

* * * * *